United States Patent
Krishnan et al.

(10) Patent No.: US 8,620,689 B2
(45) Date of Patent: Dec. 31, 2013

(54) SYSTEM AND METHOD FOR PATIENT SYNCHRONIZATION BETWEEN INDEPENDENT APPLICATIONS IN A DISTRIBUTED ENVIRONMENT

(75) Inventors: Arun Krishnan, Exton, PA (US); Venkat Raghavan Ramamurthy, Malvern, PA (US); Venkata Tumuluri, Exton, PA (US)

(73) Assignee: Seimens Medical Solutions USA, Inc., Malvern, PA (US)

( * ) Notice: Subject to any disclaimer, the term of this patent is extended or adjusted under 35 U.S.C. 154(b) by 1241 days.

(21) Appl. No.: 12/480,114

(22) Filed: Jun. 8, 2009

(65) Prior Publication Data

US 2009/0313495 A1 Dec. 17, 2009

Related U.S. Application Data

(60) Provisional application No. 61/060,902, filed on Jun. 12, 2008.

(51) Int. Cl.
*G06Q 50/00* (2012.01)

(52) U.S. Cl.
USPC .................................. 705/3; 705/2; 600/300

(58) Field of Classification Search
None
See application file for complete search history.

(56) References Cited

U.S. PATENT DOCUMENTS

| 5,235,510 | A  | * | 8/1993  | Yamada et al. | 600/300 |
| 6,807,247 | B2 |   | 10/2004 | Krishnan et al. | |
| 7,042,486 | B2 | * | 5/2006  | Manico et al. | 348/61 |
| 7,190,836 | B2 |   | 3/2007  | Krishnan et al. | |
| 2005/0068572 | A1 | * | 3/2005 | Hart et al. | 358/1.15 |

* cited by examiner

*Primary Examiner* — Michelle Le
(74) *Attorney, Agent, or Firm* — Peter R. Withstandley (57) ABSTRACT

A method for synchronizing patient data between at least two independent applications in a distributed environment includes capturing screen information from a display window of a first application client that is displaying a medical image of a patient, analyzing the screen information captured from the first application client display to extract patient identifying information, and synchronizing a display of information of the patient on a second application system display screen with the first application display window using the extracted patient identification information.

29 Claims, 8 Drawing Sheets

SYSTEM AND METHOD FOR PATIENT SYNCHRONIZATION BETWEEN INDEPENDENT APPLICATIONS IN A DISTRIBUTED ENVIRONMENT

CROSS REFERENCE TO RELATED UNITED STATES APPLICATIONS

This application claims priority from "Method for patient synchronization between independent applications in a distributed environment", U.S. Provisional Application No. 61/060,902 of Krishnan, et al., filed Jun. 12, 2008, the contents of which are herein incorporated by reference in their entirety.

TECHNICAL FIELD

This disclosure is directed to the patient data synchronization between independent applications in a distributed environment.

DISCUSSION OF THE RELATED ART

Computer-aided detection and diagnosis (CAD) are medical computer systems that assist physicians in the interpretation of medical images. Imaging modalities such as computed tomography (CT), magnetic resonance imaging (MRI), and ultrasound (US) diagnostics yield a great deal of information, which a radiologist needs to analyze and evaluate comprehensively in a short time. CAD systems help scan digital images for typical appearances and to highlight conspicuous sections, such as possible diseases. Most CAD systems generate reports in a format specified by a DICOM standard for the imaging modality used to create the image, and the organ(s) being scanned and the types of lesions being sought. Thus, there are, for example, separate DICOM standards for CT-mammography CAD structured reports, MRI colon CAD structured reports, etc.

Most CAD users prefer to do their evaluations on picture archiving and communication systems (PACS) workstations. PACS are computers or networks dedicated to the storage, retrieval, distribution and presentation of medical images. The images are stored in an independent format, typically the DICOM (Digital Imaging and Communications in Medicine) format. Integration of a CAD system on a workstation is challenging if the PACS does not natively support CAD structured reports.

A CAD system working in conjunction with a PACS is an example of independent applications interacting over a distributed environment. It is to be understood that a distributed environment need not be restricted to physically distinct machines interacting over a network, but can also be two or more virtual machines running on the same physical hardware.

Figure 1:
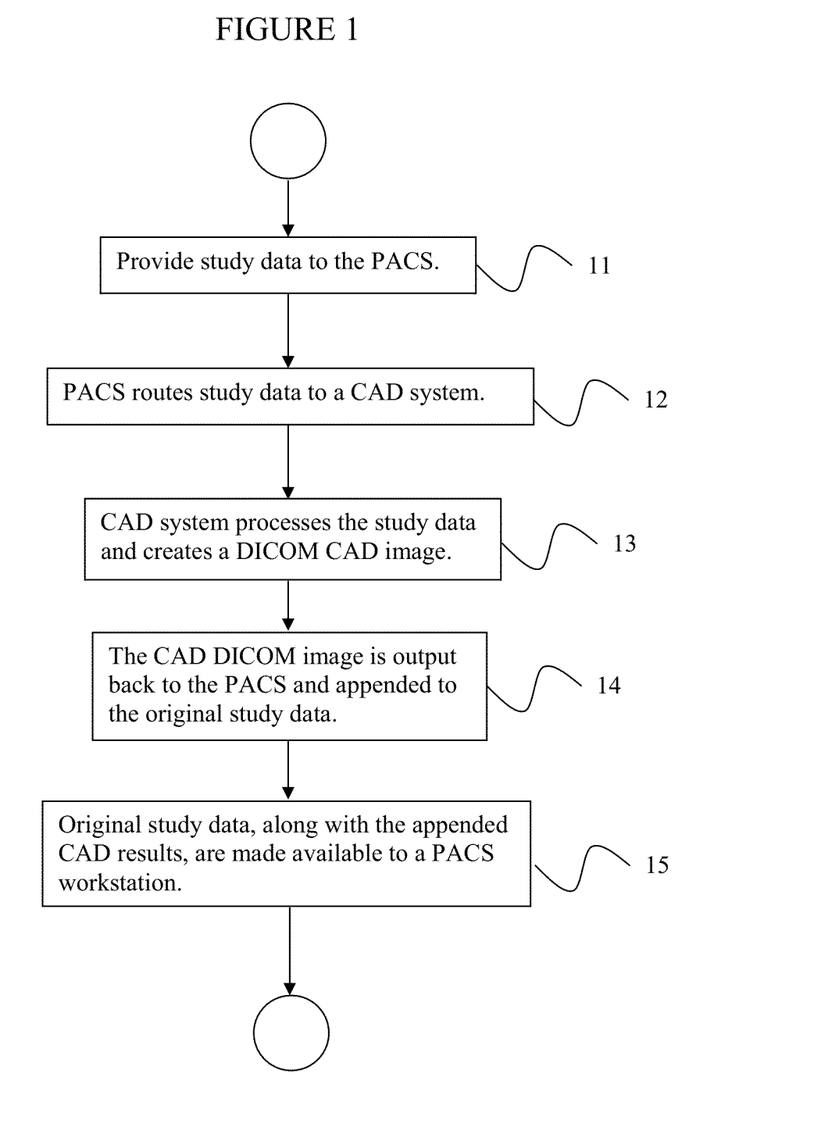
FIG. 1 illustrates a typical situation of using a CAD system with a PACS, according to an embodiment of the invention.

A typical situation of using CAD with PACS is illustrated in FIG. 1. Study data is acquired and routed to a PACS (11). The PACS routes the study data to a CAD manager (12). The data is processed by the CAD manager, which creates a DICOM CAD image (13). The CAD DICOM image is output back to the PACS and appended to the original study (14). Finally, the original study, along with the appended CAD results, are made available to a PACS workstation (15).

Sometimes, legal concerns require that the CAD information not be stored in the long term archive of a clinical site. However, there is frequently a need to review CAD marks (i.e., the locations identified by the CAD system) without any CAD information reaching the PACS database. For example, the systems disclosed in U.S. Patent Publications 2007/0192354 and 2008/0005746, include a special coding or trigger embedded in an image, which when sent to the PACS system, is recognized by a trigger response unit to launch a second application. These inventions would require sensitive data to be stored on the PACS, and would also require the installation of a trigger response unit.

Figure 2:
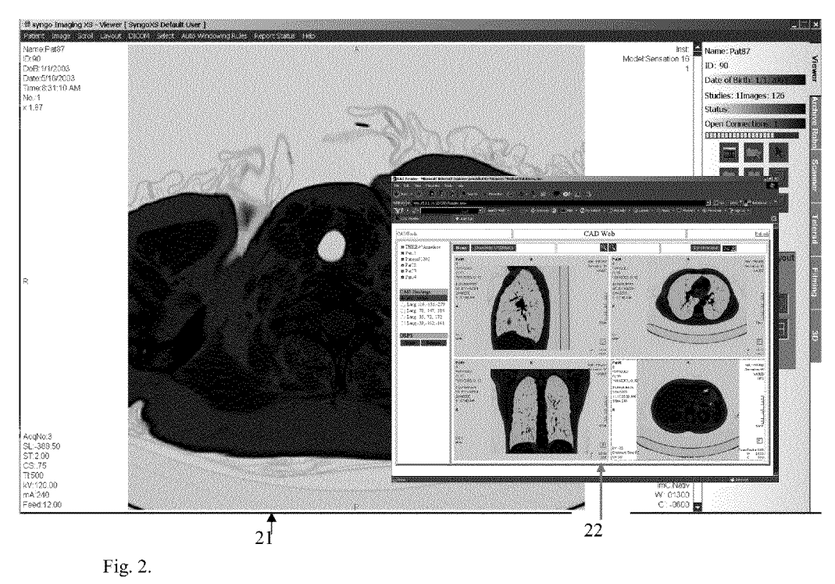
FIG. 2 depicts an example of a PACS client screen displaying one patient while a CAD webpage displays a different patient, according to an embodiment of the invention.
Figure 3:
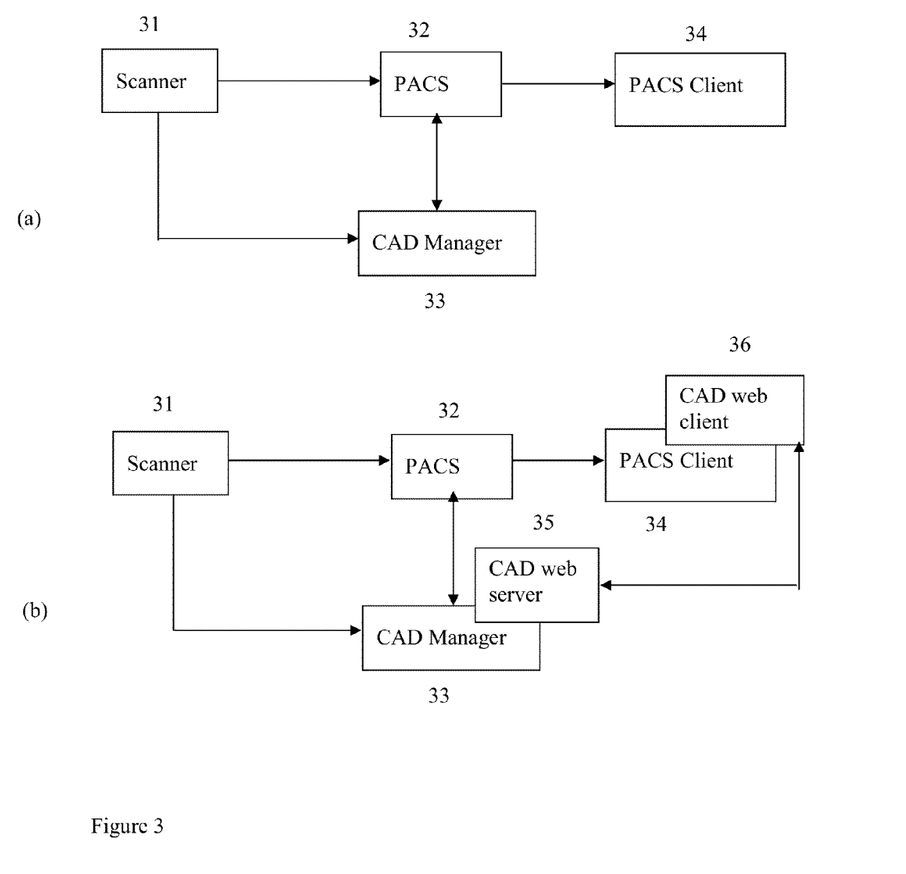
FIGS. 3(a)-(b) are block diagrams of (a) a current CAD-PACS working setup and (b) a CAD web server and web client for viewing CAD results on a PACS client without the transfer of CAD marks into the PACS system, according to an embodiment of the invention.

Although a separate CAD server will satisfy these issues, it would not resolve the issue of seeing the results on the viewing station that is used by the user. Another approach would be to use a webpage that is served from the CAD server, as depicted in FIG. 3(b), however, this would mean that while a user is reviewing the results of a Patient John Doe on the PACS, the user would have to navigate to that same patient on the web page, which points to the CAD server. FIG. 2 depicts an example of a user viewing different patients on a PACS client screen and a CAD webpage. While some PACS systems might have API's that allow the transfer of patient information to a 3rd party application, most PACS systems will not.

SUMMARY OF THE INVENTION

Exemplary embodiments of the invention as described herein generally include methods and systems for synchronizing patient data between independent applications in a distributed environment.

According to an aspect of the invention, there is provided a method for synchronizing patient data between at least two independent applications in a distributed environment, the method including capturing screen information from a display window of a first application client that is displaying a medical image of a patient, analyzing the screen information captured from the first application client display to extract patient identifying information, and synchronizing a display of information of the patient on a second application system display screen with the first application display window using the extracted patient identification information.

According to a further aspect of the invention, analyzing the screen information comprises analyzing text in the screen information for patient identifying information.

According to a further aspect of the invention, the method includes, when the captured screen information contains no text, presenting identification information for one or more previously identified patients to a user, and soliciting from the user a selection from the one or more previously identified patients.

According to a further aspect of the invention, analyzing the screen information comprises using a pixel array that is all or part of the patient image being displayed in the first application client display to determine the patient identification information by searching patient data for the pixel array across all images stored in the second application system for a block of pixels identical to the pixel array.

According to a further aspect of the invention, capturing screen information comprises photographically recording at least part of the first application display with a camera.

According to a further aspect of the invention, capturing screen information comprises shunting a signal from a display cable to the first application display to a capture device, and recording the screen information with the capture device.

According to a further aspect of the invention, the method includes transmitting the captured screen information to a second application web server for extraction of the patient identification information.

According to a further aspect of the invention, the captured screen information is encrypted.

According to a further aspect of the invention, the captured screen information is compressed.

According to a further aspect of the invention, the method includes searching for patient identification information in other open windows on the display displaying the first application window.

According to a further aspect of the invention, the method includes periodically updating the synchronization of the second application system display and the first application display.

According to a further aspect of the invention, the synchronization is updated based on a state change of at least one of the second application system display and the first application display.

According to a further aspect of the invention, the method includes designating default locations of patient identification information in the first application client.

According to a further aspect of the invention, first application is a picture archiving and communication system (PACS) and the second application is a computer-aided detection diagnosis (CAD) system.

According to another aspect of the invention, there is provided a method for synchronizing patient data between at least two independent applications in a distributed environment, the method including capturing screen information from a display window of a first application client that is displaying a medical image of a patient, designating default locations of patient identification information in the first application client, and analyzing the screen information captured from the first application client display to extract patient identifying information based on knowledge of said default locations of patient identification information.

According to a further aspect of the invention, the method includes synchronizing a display of information of said patient on a second application system display screen with said first application display window using said extracted patient identification information.

According to a further aspect of the invention, the first application is a picture archiving and communication system (PACS), and the second application is a computer-aided detection/diagnosis (CAD) system.

According to a further aspect of the invention, the method includes determining whether to display a CAD image based on a user who is logged into the CAD system and rights of this user to view the CAD image.

According to another aspect of the invention, there is provided a program storage device readable by a computer, tangibly embodying a program of instructions executable by the computer to perform the method steps for synchronizing patient data between at least two independent applications in a distributed environment.

DETAILED DESCRIPTION OF EXEMPLARY EMBODIMENTS

Exemplary embodiments of the invention as described herein generally include systems and methods for synchronizing patient data between independent applications in a distributed environment. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

FIG. 3(a) is a block diagram of (a) a current CAD-PACS working setup. Referring now to the figure, a CAD-PACS setup includes a scanner 31, which is the source of the medical image and which could be, for example, without limitation, a mammography imaging scanner, an MR scanner, a CT scanner, etc. Both the PACS 32 and the CAD manager 33 can obtain images from the scanner 31. As stated above, the PACS 32 can send study data to the CAD manager 33, the CAD manager 33 can send a processed image with appended CAD marks back to the PACS 32, and the PACS 32 can display the CAD results on a PACS client workstation 34. FIG. 3(b) is a block diagram of a system according to an embodiment of the invention for viewing CAD results on a PACS client without the transfer of CAD marks into the PACS system. A system according to an embodiment of the invention includes the addition of a CAD web server 35 and a CAD web client 36. The CAD web client 36 need not be a plug-in. Existing web browsers such as Microsoft Internet Explorer or Mozilla Firefox are non-limiting examples of a CAD web client. These browsers are usually present in the PAC client and do not need any code level changes in order to be integrated. However, the CAD web client 36 could also be a component that plugs-into the PACS client, and the CAD web client 36 need not be based on HTTP, and could use different protocols. On the CAD manager side, the CAD web server 35 could be integrated into the system either as plug-in, an HTTP server, or as a server for some other protocol.

Figure 4:
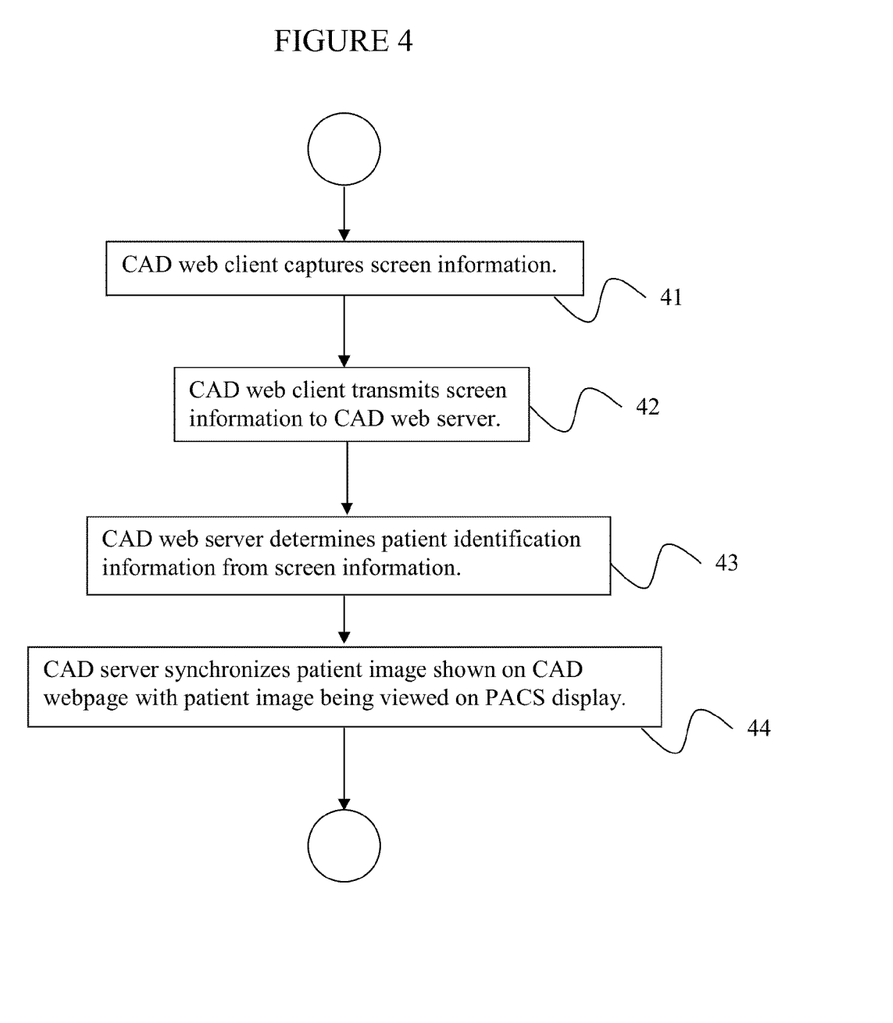
FIG. 4 is a flowchart of a method according to an embodiment of the invention for automatically synchronizing the patient being viewed on the PACS with the patient being viewed on the webpage, according to an embodiment of the invention.

A flowchart of a method according to an embodiment of the invention for automatically synchronizing the patient being viewed on the PACS with the patient being viewed on the webpage is presented in FIG. 4. Such a method would not require any explicit changes to the PACS system, or invoking APIs, and uses information already contained in the image data being viewed by the user on the PACS system to identify a patient. For example, in some cases, the image segments contain the name of the patient, patient ID, etc., as indicated by reference number 51 in FIG. 5, while in other cases, this information is on the task area (non-image segment), as indicated by reference number 61 in FIG. 6. Referring now to FIG. 4, the CAD web client captures screen information from a PACS client at step 41 and transmits it to the CAD server at step 42, possibly in an encrypted or compressed form. At step 43, the CAD server can then derive the appropriate patient identification information, using, for example, screen reading or optical character recognition. This allows the CAD server to synchronize, at step 44, the patient shown on the CAD webpage, with the patient being viewed on the PACS viewer. Thus the CAD results sent to the CAD web client would be for the same patient being viewed on the PACS viewer. The web-client does not need to re-send the whole screen-captured image to the server. It only needs to send the sub-image that contains the image text.

There are several techniques for capturing screen information. According to one embodiment of the invention, a screen shot or screen dump is used. According to another embodiment of the invention, a camera can be used to photographically record parts of the screen. According to another embodiment of the invention, the display cable going from the computer to the PACS display device can be "spliced" and this could be shunted to a capture device. The image recorded by this capture device can then be analyzed to find the patient being displayed on the PACS workstation.

Figure 5:
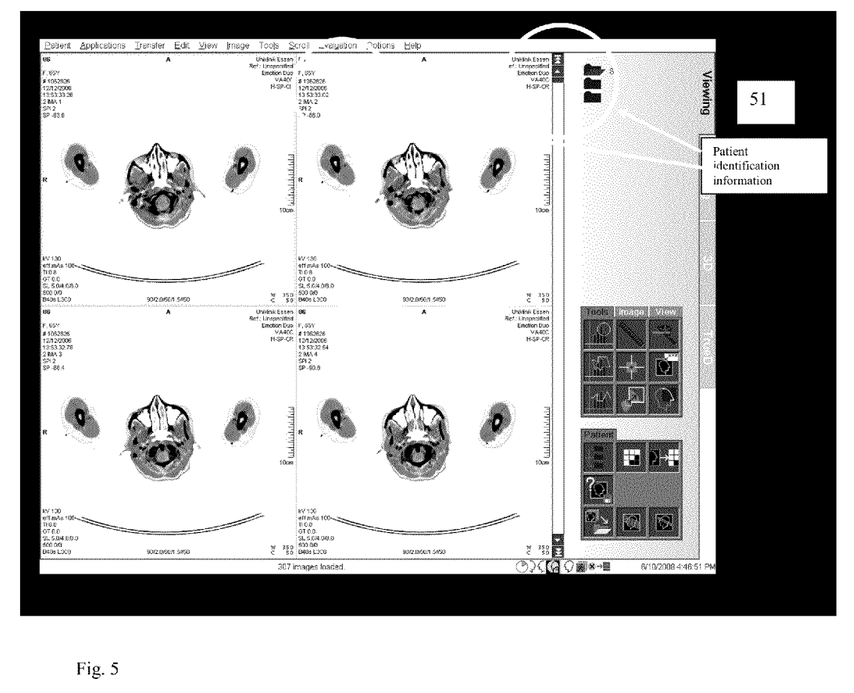
FIG. 5 is a screen shot of a PACS viewer showing patient identification information that is typically displayed, according to an embodiment of the invention.
Figure 6:
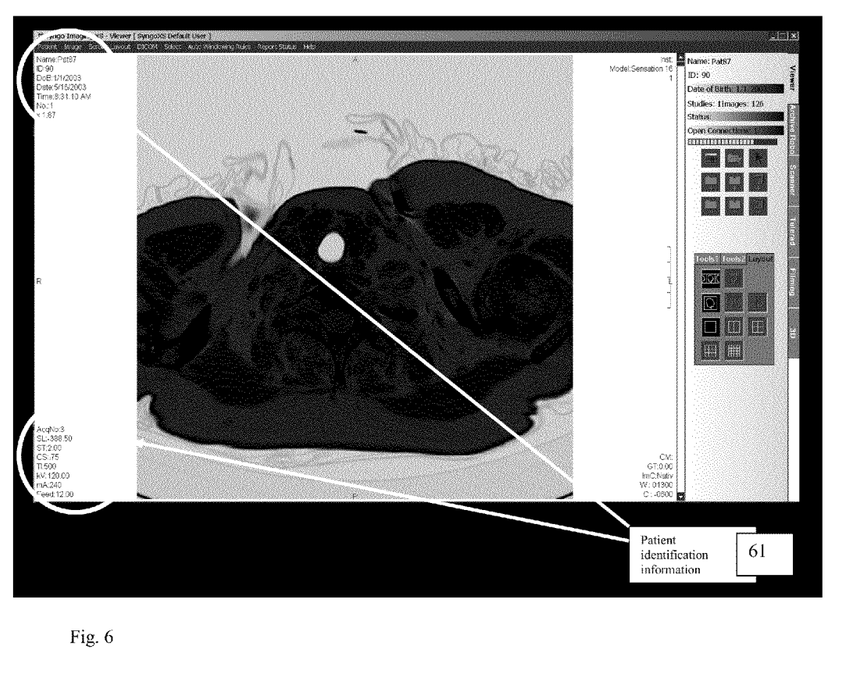
FIG. 6 is a screen shot of another PACS viewer showing patient information being displayed on the task area (non-image segment), according to an embodiment of the invention.
Figure 7:
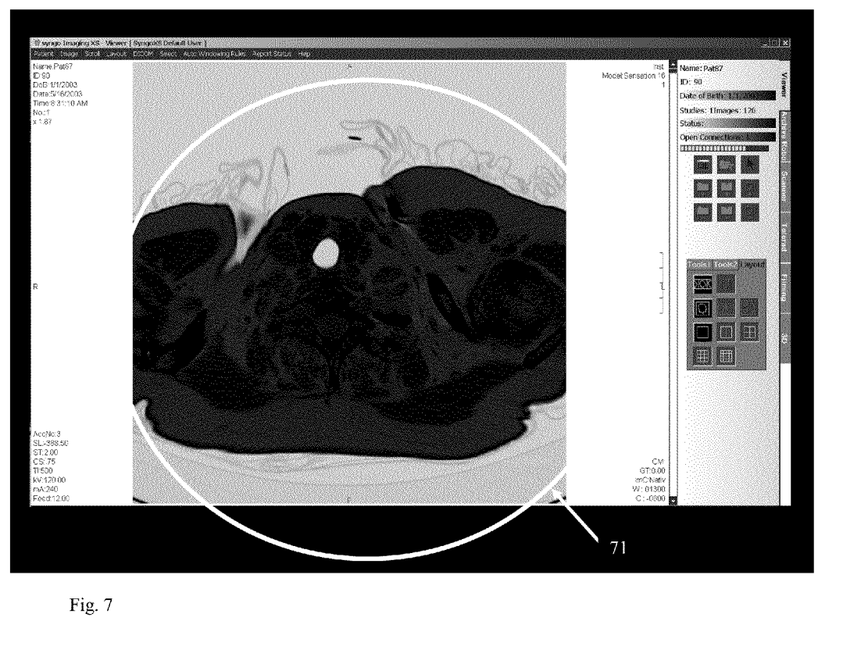
FIG. 7 illustrates how an image in combination with the particulars of how the patient data has been manipulated can also be used to identify the patient/study/series, according to an embodiment of the invention.

There are several techniques for extracting patient information from image data. According to an embodiment of the invention, text on the captured image, as shown in FIGS. 5 and 6, can be analyzed for patient identifying information. Screen reader technology can be used for this purpose, as well as optical character recognition. According to another embodiment of the invention the image shown on the PACS viewer can be used to determine the patient name. This would require a fast search of the patient data and involves searching for a given pixel array across all the volumes stored in the CAD server's database, where the pixel array is all or part of a patient image in the PACS viewer. The image in combination with the particulars of how the patient data has been manipulated (for example, Window, Center) can also be used to identify the patient/study/series, as shown in FIG. 7, where the circled region 71 indicates the image to be used for identifying the patient. The indexing would look at all patients and see which one had a block of pixels that was identical to the given pixel array, within constraints of the window/level used to go from 12 bits to 8 bits. One would hope that no more than one patient will have the identical block of pixels. This assumption will not be true if the given pixel array is small, or if the window level settings are at extremes which cause the pixel array to have an insufficient information content.

According to another embodiment of the invention, instead of only looking at the PACS viewer windows, it is also possible to look for patient information in other windows on the machine, for example, a radiology report browser. An extension would be to only look at open windows on the screen. As with the above embodiments, screen reader and optical character recognition technologies can be used for this purpose.

According to other embodiments of the invention, encryption is used for the transfer of sensitive data between the web-server and the client. In addition, according to another embodiment of the invention, the data being sent to-and-from the web-client and the server can be in compressed form. The method of compression can be done such that the most important information is prioritized higher. For example, while displaying CAD-marks on the image, the immediate area around the CAD-marks may have a higher priority than areas that are further away. The priority can be used to control the degree of compression, so that an area close to a CAD mark is loss-less, while areas further away are more heavily compressed, and to control the order of de-compression, so that areas around the CAD-marks are uncompressed and displayed to the user before the areas further away.

According to another embodiment of the invention, there can be a customization phase for a given PACS system, to designate default locations of patient identification information in the in the PACS system. The CAD web server can "learn" these default locations of the patient information text, and other relevant information. This information could include the name of the PACS viewer window handle, for those cases where the viewer window is free floating and not in a fixed location on the screen, and the different hanging protocols for the screen layout that are expected, such as, 1×1, 2×2, etc.

Some PACS viewers allow the user to modify or hide the image text that is displayed on the screen. According to another embodiment of the invention, one way to handle this situation would be for the CAD manager to remember some of the previous patients that were recognized and allow the user to choose between these patients.

The frequency of patient synchronization on the web-client, that is, how frequently the system determines which patient is being viewed on the PACS viewer and transmits this information to the CAD Server, can be based on periodic updates, a button push, or on the state of the web-client. For example, in one embodiment of the invention, a patient update can be performed based on a state change from minimized to visible in one or both of the CAD system display and the PACS system display.

Some PACS viewers allow the user to choose multiple series of images, from either the same patient of from multiple patients, to be displayed simultaneously. According to other embodiments of the invention, this can be replicated on the web-page by either showing the CAD marks of the different series simultaneously, with appropriate hanging protocols, or the user could be prompted to choose between one of the patients.

It is possible that the patient being reviewed on the PACS viewer does not exist on the CAD Server. In these cases, the patient match will fail and the web-client would not show data relevant to the patient being reviewed. It is also possible that the patient being reviewed is also present on the CAD server, but CAD processing has not finished. According to another embodiment of the invention, this could be handled, for example, with an update of the web-client page on completion of the CAD processing.

It is to be understood that while the body of this disclosure refers to a "patient", it refers to the input to the CAD processing, which can be an actual image, a series of images, a study, etc. Furthermore, while the disclosure describes synchronization with a web-client showing CAD results, one of skill in the art will understand that a method according to an embodiment of the invention could also be used to synchronize patients across different applications, such as synchronization between PACS and RIS, etc. or to send segmentation results from the server to the web-client. In addition, one of skill in the art will understand that a web-client can be replaced by other technologies that have similar user benefits.

User privileges and user rights can also be considered. For example, the CAD server could determine whether or not a CAD mark should be displayed based on (1) the user who is logged into the CAD server via the web client, and (2) the rights of this user to view the CAD marks. For example, a reading physician would be able to see all the CAD marks, while a referring physician might only be able to see those marks that have been added by the reading physician.

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 8:
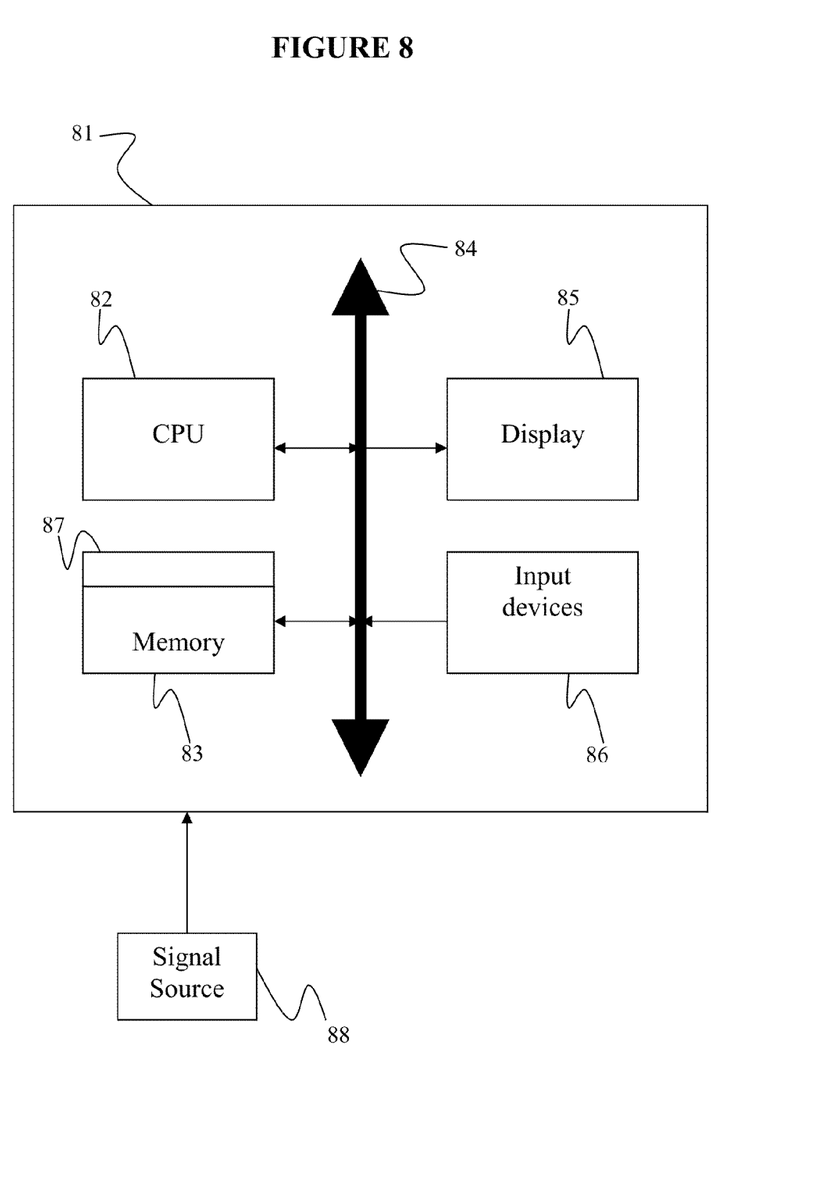
FIG. 8 is a block diagram of an exemplary computer system for implementing a method for synchronizing patient data between independent applications in a distributed environment, according to an embodiment of the invention.

FIG. 8 is a block diagram of an exemplary computer system for implementing a method for synchronizing patient data between independent applications in a distributed environment, according to an embodiment of the invention. Referring now to FIG. 8, a computer system 81 for implementing the present invention can comprise, inter alia, a central processing unit (CPU) 82, a memory 83 and an input output (I/O) interface 84. The computer system 81 is generally coupled through the I/O interface 84 to a display 85 and various input devices 86 such as a mouse and a keyboard. The support circuits can include circuits such as cache, power supplies, clock circuits, and a communication bus. The memory 83 can include random access memory (RAM), read only memory (ROM), disk drive, tape drive, etc., or a combinations thereof. The present invention can be implemented as a routine 87 that is stored in memory 83 and executed by the CPU 82 to process the signal from the signal source 88. As such, the computer system 81 is a general purpose computer system that becomes a specific purpose computer system when executing the routine 87 of the present invention.

The computer system 81 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A computer implemented method for synchronizing patient data between at least two independent applications in a distributed computing environment, the method comprising the steps of:
   capturing, by a computer system, screen information from a display window of a first application client that is displaying a medical image of a patient on a screen, wherein the first application is a picture archiving and communication system (PACS);
   analyzing, by the computer system, the screen information captured from the first application client display to extract patient identifying information; and
   synchronizing, by the computer system, a display of computer-aided detection diagnosis (CAD) information of said patient in a second application system display window on the screen along with said first application display window using said extracted patient identification information;
   wherein said second application is a computer-aided detection diagnosis (CAD) system.

2. The method of claim 1, wherein analyzing said screen information comprises analyzing text in said screen information for patient identifying information.

3. The method of claim 2, further comprising, when said captured screen information contains no text, presenting identification information for one or more previously identified patients to a user, and soliciting from said user a selection from said one or more previously identified patients.

4. The method of claim 1, wherein analyzing said screen information comprises using a pixel array that is all or part of said patient image being displayed in the first application client display to determine the patient identification information by searching patient data for said pixel array across all images stored in said second application system for a block of pixels identical to said pixel array.

5. The method of claim 1, wherein capturing screen information comprises photographically recording at least part of the first application display with a camera.

6. The method of claim 1, wherein capturing screen information comprises shunting a signal from a display cable to the first application display to a capture device, and recording the screen information with said capture device.

7. The method of claim 1, further comprising transmitting said captured screen information to a second application web server for extraction of the patient identification information.

8. The method of claim 7, wherein said captured screen information is encrypted.

9. The method of claim 7, wherein said captured screen information is compressed.

10. The method of claim 1, further comprising searching for patient identification information in other open windows on the display displaying the first application window.

11. The method of claim 1, further comprising periodically updating said synchronization of said second application system display and said first application display.

12. The method of claim 11, wherein said synchronization is updated based on a state change of at least one of the second application system display and said first application display.

13. The method of claim 1, further comprising designating default locations of patient identification information in the first application client.

14. A computer implemented method for synchronizing patient data between at least two independent applications in a distributed computing environment, the method comprising the steps of:
 capturing, by a computer system, screen information from a display window of a first application client that is displaying a medical image of a patient;
 designating, by the computer system, default locations of patient identification information in the first application client; and
 analyzing, by the computer system, the screen information captured from the first application client display to extract patient identifying information based on knowledge of said default locations of patient identification information;
 wherein said first application is a picture archiving and communication system (PACS) and said second application is a computer-aided detection diagnosis (CAD) system.

15. The method of claim 14, further comprising synchronizing a display of information of said patient on a second application system display screen with said first application display window using said extracted patient identification information.

16. The method of claim 14, further comprising determining whether to display a CAD image based on a user who is logged into the CAD system and rights of this user to view the CAD image.

17. A non-transitory program storage device readable by a computer, tangibly embodying a program of instructions executable by the computer to perform the method steps for synchronizing patient data between at least two independent applications in a distributed environment, the method comprising the steps of:
 capturing screen information from a display window of a first application client that is displaying a medical image of a patient;
 analyzing the screen information captured from the first application client display to extract patient identifying information; and
 synchronizing a display of information of said patient on a second application system display screen with said first application display window using said extracted patient identification information;
 wherein said first application is a picture archiving and communication system (PACS) and said second application is a computer-aided detection/diagnosis (CAD) system.

18. The computer readable program storage device of claim 17, wherein analyzing said screen information comprises analyzing text in said screen information for patient identifying information.

19. The computer readable program storage device of claim 18, the method further comprising, when said captured screen information contains no text, presenting identification information for one or more previously identified patients to a user, and soliciting from said user a selection from said one or more previously identified patients.

20. The computer readable program storage device of claim 17, wherein analyzing said screen information comprises using a pixel array that is all or part of said patient image being displayed in the first application client display to determine the patient identification information by searching patient data for said pixel array across all images stored in said second application system for a block of pixels identical to said pixel array.

21. The computer readable program storage device of claim 17, wherein capturing screen information comprises photographically recording at least part of the first application display with a camera.

22. The computer readable program storage device of claim 17, wherein capturing screen information comprises shunting a signal from a display cable to the first application display to a capture device, and recording the screen information with said capture device.

23. The computer readable program storage device of claim 17, the method further comprising transmitting said captured screen information to a second application web server for extraction of the patient identification information.

24. The computer readable program storage device of claim 23, wherein said captured screen information is encrypted.

25. The computer readable program storage device of claim 23, wherein said captured screen information is compressed.

26. The computer readable program storage device of claim 17, the method further comprising searching for patient identification information in other open windows on the display displaying the first application window.

27. The computer readable program storage device of claim 17, the method further comprising periodically updating said synchronization of said second application system display and said first application display.

28. The computer readable program storage device of claim 27, wherein said synchronization is updated based on a state change of at least one of the second application system display and said first application display.

29. The computer readable program storage device of claim 17, the method further comprising designating default locations of patient identification information in the first application client.

* * * * *